United States Patent [19]
Morris

[11] Patent Number: 4,701,419
[45] Date of Patent: Oct. 20, 1987

[54] ANALYSIS OF POLYMERIC PROTEIN AND PROTEIN PRODUCTS

[75] Inventor: Howard R. Morris, Iver, United Kingdom

[73] Assignee: M-Scan Limited, Berkshire, England

[21] Appl. No.: 801,970

[22] Filed: Nov. 26, 1985

[30] Foreign Application Priority Data

Nov. 26, 1984 [GB] United Kingdom ............... 8429846

[51] Int. Cl.4 ........................................... G01N 33/68
[52] U.S. Cl. ..................................... 436/89; 436/15;
   436/175; 435/23; 435/24; 250/282
[58] Field of Search .................... 436/15, 89, 173, 175;
   250/282; 435/23, 24

[56] References Cited

U.S. PATENT DOCUMENTS

| | | | |
|---|---|---|---|
| 3,959,307 | 5/1976 | Wittmann | 436/89 |
| 4,065,412 | 12/1977 | Dreyer | 436/89 |
| 4,224,031 | 9/1980 | Mee et al. | 436/173 |
| 4,554,254 | 11/1985 | Krystal | 436/175 |

FOREIGN PATENT DOCUMENTS

| | | |
|---|---|---|
| 1193255 | 5/1966 | United Kingdom . |
| 1304938 | 1/1973 | United Kingdom . |
| 1360731 | 7/1974 | United Kingdom . |
| 2049191 | 12/1980 | United Kingdom ............... 436/173 |
| 2091937 | 8/1982 | United Kingdom . |

OTHER PUBLICATIONS

Miller, M. J., Loudon, G. M., J Am Chem Soc (U.S.A.), vol. 97, No. 18, U.S.A. 23–230M, Sep. 3, 1975.

*Primary Examiner*—S. Leon Bashore
*Assistant Examiner*—Lori-Ann Cody
*Attorney, Agent, or Firm*—Sandler & Greenblum

[57] ABSTRACT

Methods are provided for determining the presence or absence of ragged ends in polymeric proteins or protein products, by means of fast atom bombardment and high mass mass spectrometry (preferably high field magnet mass spectrometry). The methods may be modified for locating N- or C-terminal peptide in a polymeric protein or protein product and for assigning disulphide bridges in polymeric protein or protein products. The methods are applicable to other biopolymers such as nucleotides and carbohydrates.

19 Claims, 1 Drawing Figure

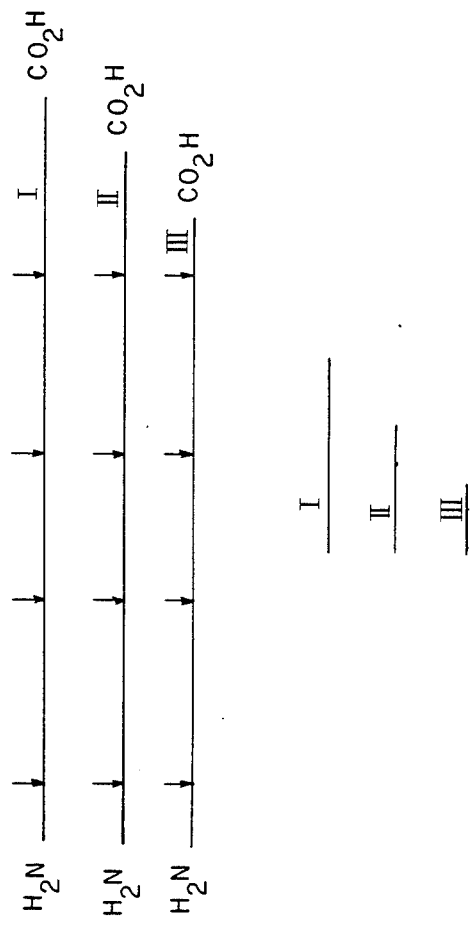

ANALYSIS OF POLYMERIC PROTEIN AND PROTEIN PRODUCTS

This invention relates to a method of analysing a polymeric protein or protein product for the presence or absence of a 'ragged end' at its C-terminus and/or N-terminus. The invention is also capable of locating and identifying microheterogeneity in recombinant protein products, and capable of assigning disulphide bridges.

When producing a protein product by means, for example, of recombinant DNA biotechnology, it is possible for the protein product produced to be shorter or longer than expected due to one or more amino acids in the amino acid sequence being missing from or added to either the N-terminus, or, more usually, the C-terminus of the protein product. Such a deficiency is referred to as a 'ragged end'. The absence or addition of such amino acids can effect the usefulness or acceptability of the protein product so it is important to know whether such a ragged end exists and to know the constitution of the end portion(s) of the protein product.

The traditional method for ascertaining the structure of a polymeric protein is to degrade the polymer into component parts, to isolate and purify each part and then to perform structural studies upon each part by stepwise chemical degradation (edman degradation). This work is extremely time-consuming because of the purification steps required, and moreover, suffers from the following difficulties;

(1) inability to cope with blocked N-terminal proteins or peptides,
(2) the inability to identiy new post-translational modifications, insertions, deletions, or chemical changes such as phosphorylation or glycosylation,
(3) difficulty in assigning C-terminal sequences i.e. at the end of the molecule opposite to where degradation is being effected.

In fact if a mixture of proteins, is being analysed, the method cannot be used to reliably derive complete information about the N- or C-terminus.

It ahs been suggested to perform mass-spectrometric analysis of proteins using fast atom bombardment analysis in a high mass or a high field magnet mass spectrometer but there has been no suggestion that these techniques can be used to look for ragged ends at the N-or C-terminus in the protein or protein product, or to detect microheterogeneity in proteins or to assign disulphide bridges.

According to a first aspect of the present invention there is provided a method of analysing a polymeric protein or protein product for the presence or absence of a ragged end (as hereinbefore defined at its C- or N-terminus which method comprises the steps of:

(a) carrying out a chemical or enzymatic digestion upon a polymeric protein or protein product to produce N- or C-terminus fragments which are differentiable from non-terminal fragments of the digested protein or protein product;
(b) subjecting the N- and/or C-terminus fragments obtained to fast atom bombardment and high mass mass spectrometry;
(c) analysing the mass spectrometric data obtained and checking for the occurrence of fragments having a mass which would be unexpected from a study of a known complete molecule of the protein or protein product which is believed to be present, the occurrence of such unanticipated fragments indicating the presence of a ragged end.

A similar methodology can be used to detect unanticipated protein fragments which indicate the presence of microheterogeneity or of blocking or of post-translational groups.

The term "differentiable" employed in the foregoing definition of the invention is intended to mean that the respective terminal and non-terminal fragments are clearly distinguishable from each other by mass spectrometric techniques. The terminal fragments may be distinguished from non-terminal fragments either on the basis that terminal fragments are likely to be considerably smaller than non-terminal fragments, e.g. $\frac{1}{2}$ to $\frac{1}{3}$ of their mass, or on the basis of expected mass where the expected composition of the protein or protein product is known and the results of digestion can therefore be predicted.

The above invention is most useful for checking the consitution of a protein or protein product where the amino acid sequence of the 'whole' protein or protein product which is believed to be present is known. The invention is also utilizable in those cases where the complete amino-acid sequence of the N- and/or the C-terminus is unknown.

The foregoing invention can be extended so that not only can the mass of the terminus fragment be determined but also the amino acid sequence of that fragment. In general any specific mass is almost unique to a particular group of specific amino-acids. The specific sequence of the amino acids within the fragment can be determined by further digestion of the protein using a different digestion agent causing cleavage at different sites and hence the formation of subfragments.

Sometimes the step of fast atom bombardment and high field magnet mass spectrometry will cause the terminal fragments to break-up and produce ionic subfragments. The masses of the ionic subfragments can be used to assess the make up and sequence of the amino acid residues in the terminal fragment. In such a case there would be no need for the further digestion step referred to above.

Sometimes the mass of a fragment may convey ambiguous information about the amino acid content of the peptide fragment; in such a case a further digestion to produce smaller peptide fragments or a digestion of further starting material using a different digestion technique (such as CNBr, Edman or endo- or exopeptidases) to produce cleavage at different sites, can resolve the ambiguity. Information can also be obtained by analysis of a chemical derivative or by measurement of the accurate mass of the peptide fragments, e.g. by standard methods, to resolve the ambiguity.

According to a second aspect of the present invention there is provided a method for locating the N- or C-terminal peptide in a polymeric protein or protein product which method comprises the steps of:

(a) carrying out a chemical or enzymatic digestion upon a product to produce N- or C-terminus fragments which are differentiable (as hereinbefore defined) from non-terminal fragments, of the digested protein or protein product;
(b) subjecting the protein fragments obtained to fast atom bombardment and high mass mass spectrometry;
(c) carrying out a second and different digestion upon the products of step (a);

(d) subjecting the protein fragments of step (c) to fast atom bombardment and high mass mass spectrometry; and (e) analysing and comparing the mass spectrometric data obtained from both mass spectrometric exercises to establish whether or not some or all of the mass spectrometric signal peaks have shifted and deducing from this the location of the terminal peptide.

In addition to location of the terminal peptide it is possible to identify all of the amino acid residues in the terminal fragment and to work out the sequence of those amino acid residues in the terminal fragment. This is achieved by conducting an additional digestion to remove a final amino acid residue from the terminal fragment using e.g. an Edman degradation or an exopeptidase, such as carboxypeptidase Y, together with fast atom bombardment and high mass mass spectrometry, before the digestion step (a) of the second aspect of the present invention. The effect of this extra digestion is to remove the final amino acid residue and allow it to be individually identified from the mass spectrometric results. This step can be repeated several times to identfy the sequence of the amino acid resides in the terminal fragment. In can be performed to identify the sequence at either the N-terminus or at the C-terminus.

Any suitable chemical or enzymatic digestion may be employed in step (a) of the present invention, such digestion being directed at one or more specific sites. Examples of suitable digestions are by the use of trypsin, chymotrypsin, cyanogen bromide, carboxypeptidase A, carboxypeptidase B or carboxypeptidase Y and by the use of Edman degradation using phenyl isothiocyanate followed by cleavage with trifluoracetic acid. To bring the protein or protein product molecule into the effective routine mass range of the high mass mass spectrometer, a reduction step can be carried out, e.g. by using dithiothreitol followed, if necessary, by alkylation, acidification, desalting and elution.

According to a third aspect of the present invention there is provided a method of assigning disulphide bridges in polymeric protein or protein products which method comprises the steps of:

digesting a protein or protein product in an unreduced state;

subjecting the digest mixture or one or more fractionated components thereof to fast atom bombardment and high mass mass spectrometry;

treating the digest mixture or, one or more of fractionated components to a molecular weight altering step; and performing mass spectrometric analysis upon the treated products and comparing the mass spectrometric results to identify disulphide bridged peptides by their characteristic masses. The interpretation may be effected by steps of subdigestion and/or reduction and/or Edam degradation and further fast atom bombardment and high mass mass spectrometry. The method can also be used to study the dynamics of protein denaturation/renaturation and the dynamics of protein folding. It is to be understood that peptides resulting from a reduced disulphide bridge will have characteristic mass whilst the unreduced disulphide bridge will have a weight of the added masses less 2, this discrepancy resulting from the presence or absence of two hydrogen atoms.

A preferred technique for conducting enzymatic digestion is to subject from 10 picomoles to 50 nanomoles of the protein to the enzyme, such as trypsin, in a 50 millimolar ammonium bicarbonate bufer at pH 8.5 with an enzyme: substrate ratio of 1:50 for from 1 to 3 hours at 37° C. or to an enzyme such as pepsin in 5% formic acid for 6 hrs.

A preferred technique for conducting an Edman degradation is to subject the protein or protein product to treatment with phenyl isothiocyanate at pH 8.5 at 65° C. for 1 hour followed by cleavage with trifluoroacetic acid at 65° C. for 10 minutes. This degradation can be repeated as many times as necessary until the peptides have been shortened to the required length, this length being monitored and assigned by means of fast atom bombardment and high mass mass spectrometry.

Preferably the high mass mass spectrometry is high field magnet mass spectrometry although any other suitable mass spectrometric technique or instrument may be employed, such as a time of flight instrument using Californium 252 fission bombardment.

The fast atom bombardment and high mass mass spectrometry is preferably carried out using apparatus such as a VG ZAB HF or SE instrument preferably equipped with an M-SCAN fast atom bombardment gun, using Xenon or cesium as the primary ionising beam (current of 20 $\mu$A at 8 KeV). Samples of a size 10 picomoles to 5 nanomoles in 2 $\mu$l of 5% acetic acid are preferably loaded onto a glycerol coated probe tip preferably followed by 1 $\mu$l of thioglycerol. The fast atom bombardment and high field magnet mass spectrometry may be carried out directly upon the protein digest or after separation by any suitable technique such as by using gel permeation chromatography or by using high pressure liquid chromatography.

The accompanying diagram, which illustrates schematically complete and incomplete protein products, indicates how selective cleavage of the protein products can be used to determine the presence of 'ragged ends'.

The topmost protein molecule in the diagram may be regarded as complete; therefore selective cleavage near the C-terminus will produce a peptide fragment (I) of known predictable mass. Such selective cleavage may be effected by any suitable specific cleaving agent e.g. by enzymes or chemically; the method employed in the example was to use cyanogen bromide which cleaves the peptide bond whose carbonyl function is contributed by a methionine (MET) residue.

If the protein or protein product is not complete at its C-terminus (i.e. if it has undergone proteolytic nicking) as in the middle and lower molecules illustrated schematically in the diagram, then cleavage will produce other peptide fragments (II) and (III) whose masses would not be anticipated if only complete protein or protein product was present. The presence of the additional fragments II and III will thus reveal the presence of ragged ends and allow the degree of proteolytic nicking to be ascertained. These fragments may be quantified either by carboxypeptidase B analysis of the intact proteins or by prior separation of the above assigned fragments combined with usch methods as uV analysis and fast atom bombardment mass spectrometry or amino-acid analysis.

As an example of the location and identification of a terminal fragment, a protein was digested under conditions as set out above with trypsin to cleave those peptide bonds in which the carboxyl derives from lysine (LYS) or arginine (ARG).

The resultant digest was subjected without separation to fast atom bombardment and high field magnet mass spectrometry using the preferred apparatus and conditions described above.

Subsequently a disgestion was carried out upon the tryptic digest using carboxypeptidase B (which cleaves terminal LYS or ARG amino acid residues which are not adjacent to proline (PRO)) under the above-mentioned preferred conditions and further fast atom bombardment and high field magnet mass spectrometry was effected, again using the preferred apparatus and conditions.

A comparison of the spectrometric data of the respective digests shows that all masses shift by either 128(LYS) or 156(ARG) mass units except the C-terminal peptide or peptides terminating in PRO-ARG or PRO-LYS thus allowing location and characterization of the C-terminal peptide. If all the signals shift this indicates that the whole protein terminates in LYS or ARG or that a peptide is missing.

The method of the present invention is more precise, much quicker (and hence less expensive) than existing traditional techniques, and can be conducted quantitatively. It allows gene products to be screened rapidly for errors of translation, mutation, deletions and insertions and may be used for routing quality control.

Although the invention has been described with reference to proteins and protein products, it is envisaged that it may have applicability to other biopolymers such as nucleotides and carbohydrates.

I claim:

1. A method of analyzing a polymeric protein or polymeric protein product for the presence or absence of a ragged end at its C-or N-terminus, said method comprising the steps of:
   (a) digesting chemically or enzymatically said polymeric protein or polymeric protein product to produce N- or C-terminus fragments which are differentiable from non-terminal fragments of te digested protein or protein product;
   (b) subjecting the N- and/or C-terminus fragments obtained in step (a) to fast atom bombardment and high-mass mass spectrometry; and
   (c) analyzing the mass spectrometric data obtained and checking for the presence of fragments having a mass which would be unexpected from a study of a known complete molecule of the protein or protein product which is believed to be present, whereby the presence of such unexpected fragments indicates the presence of said ragged end.

2. The method according to claim 1, wherein said chemical digestion is carried out by using chemicals selected from the group consisting of (a) phenyl isothiocyanate followed by cleavage with triflouracetic acid, and (b) CNBr.

3. The method according to claim 1, wherein said enzymatic digestion is carried out by using an enzyme selected from the group consisting of trypsin, chymotrypsin, carboxypeptidase A, carboxypeptidase B, and carboxypeptidase Y.

4. The method according to claim 1, wherein a preliminary reduction is effected upon the protein or protein product, to bring the protein or protein product molecules into the effective routine mass range of the high-mass mass spectrometer.

5. The method according to claim 1, wherein steps (a) to (c) are repeated upon said protein or protein product using a second and different digestion thereby causing cleavage at different sites and hence forming subfragments.

6. The method according to claim 1, wherein fast atom bombardment is effected by using, as the primary ionising beam, atoms selected from the group consisting of Xenon atoms and cesium atoms.

7. The method according to claim 1, wherein the high-mass mass spectrometry comprises high field magnet mass spectrometry.

8. The method according to claim 1, wherein the high-mass mass spectrometry comprises Californium 252 fission bombardment.

9. The method according to claim 1, wherein said polymeric protein in interferon.

10. The method according to claim 1, wherein said polymeric protein is insulin.

11. A method for locating the N- or C-terminal peptide in a polymeric protein or protein product, said method comprising the steps of:
    (a) digesting chemically or enzymatically said polymeric protein or polymeric protein product to produce N- or C-terminus fragments which are differentiable from non-terminal fragments, of the digested protein or protein product;
    (b) subjecting the protein fragments obtained in step (a) to fast atom bombardment and high-mass mass specrometry;
    (c) subjecting the products obtained in step (a) to a second digestion step, said second digestion step being different from said first chemical or enzymatic digestion;
    (d) subjecting the protein fragments of step (c) to fast atom bombardment and high-mass mass spectrometry; and
    (e) analyzing and comparing the mass spectrometric data obtained from both mass spectrometric exercises of steps (b) and (d) to establish whether or not some or all of the mass spectrometric signal peaks have shifted, and deducing from this the location of the terminal peptide.

12. The method according to claim 11, wherein said polymeric protein is interferon.

13. The method according to claim 11, wherein said polymeric protein is insulin.

14. A method of assigning disulphide bridges in polymeric protein or polymeric protein products, said method comprising the steps of:
    (a) digesting said protein or protein product in an unreduced state;
    (b) subjecting the digest mixture or, one or more fractionated components thereof to fast atom bombardment and high-mass mass spectrometry;
    (c) treating the digest mixture or, one or more fractionated components thereof to a molecular-weight altering step; and
    (d) performing mass spectrometric analysis upon the products obtained in step (c) and comparing the mass spectrometric results to identify disulphide bridged peptides by their characteristic masses.

15. The method according to claim 1, 11 or 14, which is carried out upon a nucleotide or a carbohydrate instead of upon a polymeric protein or protein product.

16. The method according to claim 14, wherein said molecular weight altering step is a reduction step of adding hydrogen atoms to the digest mixture or fractionated components obtained in step (c).

17. The method according to claim 14, wherein said molecular weight altering step is a subdigestion step.

18. The method according to claim 14, wherein said polymeric protein is interferon.

19. The method according to claim 14, wherein said polymeric protein is insulin.

* * * * *

UNITED STATES PATENT AND TRADEMARK OFFICE
CERTIFICATE OF CORRECTION

PATENT NO. : 4,701,419

DATED : October 20, 1987

INVENTOR(S) : Howard R. MORRIS

It is certified that error appears in the above-identified patent and that said Letters Patent is hereby corrected as shown below:

At column 1, line 28 change "edman" to ---Edman---.
At column 1, line 31 change ";" to ---:---.
At column 1, line 34 change "identiy" to ---identify---.
At column 1, line 43 change "ahs" to ---has---.
At column 1, line 54 insert ---)--- after "defined".
At column 3, line 24 change "identfy" to ---identify---.
At column 3, line 25 change "In" to ---It---.
At column 4, line 61 change "usch" to ---such---.
At column 5, line 5 change "disgestion" to ---digestion---.
At column 5, line 38 change "te" to ---the---.
At column 6, claim 11, line 24 change "specrometry" to ---spectrometry---.

Signed and Sealed this

Thirteenth Day of September, 1988

Attest:

DONALD J. QUIGG

Attesting Officer

Commissioner of Patents and Trademarks